United States Patent [19]

Demos

[11] Patent Number: 4,784,139

[45] Date of Patent: Nov. 15, 1988

[54] NEEDLE GUIDE INSTRUMENT

[76] Inventor: Nicholas J. Demos, 4 Cambridge Dr., Short Hills, N.J. 07078

[21] Appl. No.: 877,219

[22] Filed: Jun. 23, 1986

[51] Int. Cl.⁴ ............................................. A61B 17/06
[52] U.S. Cl. ..................................... 128/340; 128/339
[58] Field of Search .................. 604/272; 128/340, 339

[56] References Cited

U.S. PATENT DOCUMENTS

| | | | |
|---|---|---|---|
| 2,833,284 | 5/1958 | Springer | 128/340 |
| 2,897,820 | 8/1959 | Tauber | 128/340 |
| 2,973,761 | 3/1961 | Kohl | 128/346 |
| 3,491,756 | 1/1970 | Bentov | 128/334 R |
| 4,349,027 | 9/1982 | DiFranceso | 128/340 |

OTHER PUBLICATIONS

Publication entitled, "A Plastic Needle", by Dr. David J. Massa et al., published Jul. 5, 1980.

Primary Examiner—Richard C. Pinkham
Assistant Examiner—Gary Jackson
Attorney, Agent, or Firm—Stoll, Wilkie, Previto & Hoffman

[57] ABSTRACT

A surgical instrument having a suture needle guide at one end and an instrument gripping and guiding handle at the other end. The instrument has a general longitudinal axis. The handle is elongated and curved along its length away from the longitudinal axis to facilitate gripping and the needle guide has an exposed concave surface to underlie and guide the needle as it is passed into the surface to be sutured.

2 Claims, 1 Drawing Sheet

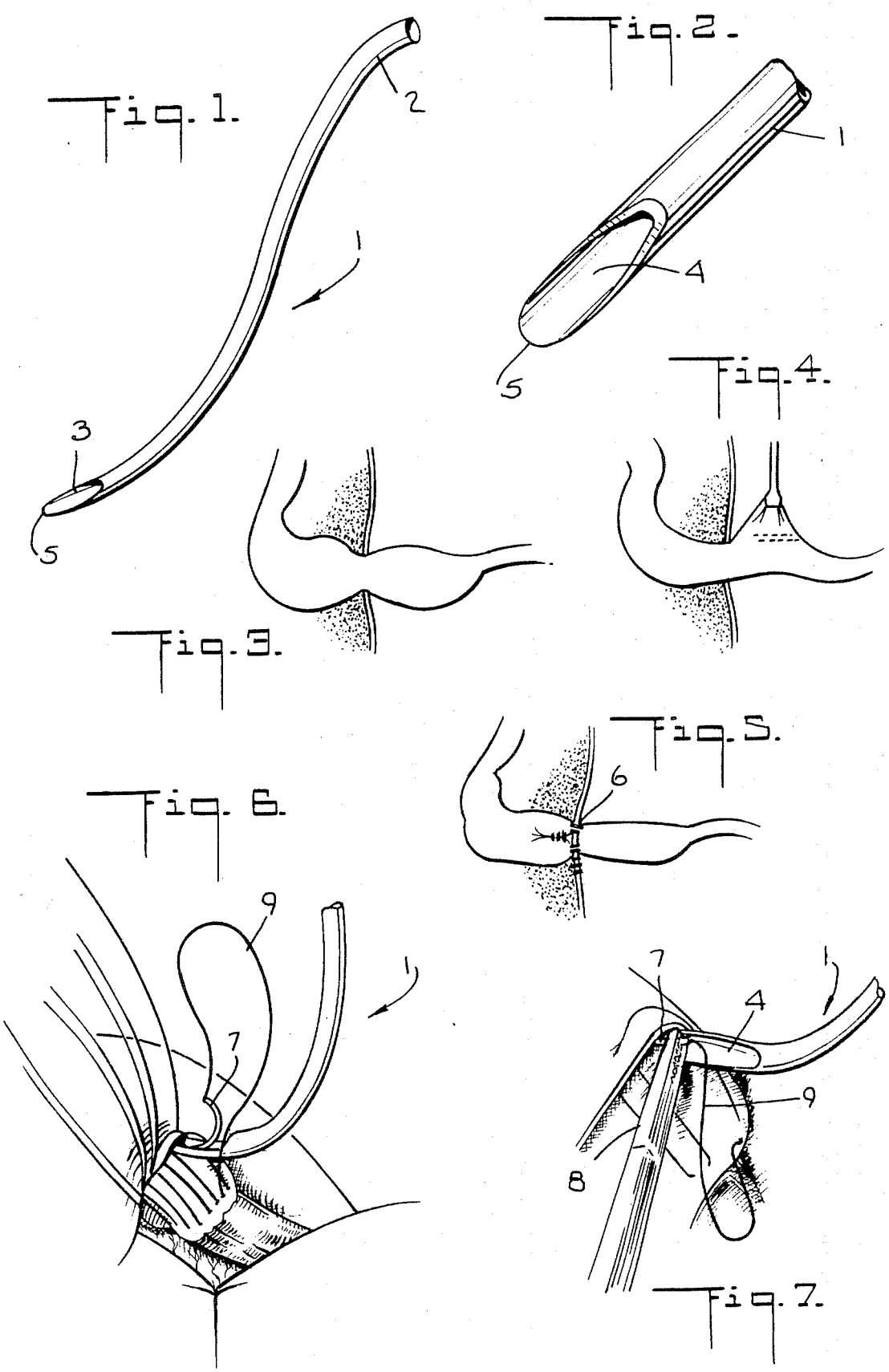

NEEDLE GUIDE INSTRUMENT

BACKGROUND OF THE INVENTION

The present invention relates to a surgical instrument and more particularly to a needle guide which permits surgeons to locate and insert sutures in confined areas thereby minimizing the amount of cutting necessary during the surgical procedure.

There are a number of surgical procedures where a principal drawback or disadvantage results not from the actual suturing or the immediate surgical operation, but from the necessity to do relatively extensive cutting to expose the sutured area for the surgery.

An important example of this occurs in hiatal hernia operations where the use of the needle guide eliminates the need for any significant cutting of gastroplasty. The needle guide may be slipped into a confined area where the suturing is performed with the needle guide being easily and properly positioned thereby positioning the suture needle.

Accordingly, an object of the present invention is to provide an improved instrument for surgery.

Another object of the present invention is to provide an improved needle guide for suturing in surgery performed in confined locations, such as the pelvis during low anterior rectal anastomosis or other pelvic procedures.

Another object of the present invention is to provide an improved surgical instrument for use in hiatal hernia operations.

Another object of the present invention is to provide a surgical means for substantially eliminating cutting of gastroplasty in hernia operations.

Other and further objects of the present invention will be apparent upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

A preferred embodiment of the invention has been chosen for purposes of illustration and description and is shown in the accompanying drawings, forming a part of the specification wherein:

FIG. 1 is a perspective view of a needle guide in accordance with the invention.

FIG. 2 is an enlarged fragmentary perspective view of the needle guiding end of the needle guide of FIG. 1.

FIGS. 3 thru 5 are diagrammatic successive views in section of a hiatal hernia procedure.

FIGS. 6 and 7 are perspective views illustrating successive steps in inserting sutures using the guide of the invention.

DESCRIPTION OF THE PREFERRED EMBODIMENT

As illustrated in FIGS. 1 and 2, the needle guide 1 of the invention comprises an elongated relatively thin instrument of convenient length for manipulation with a typical overall length of about 12 inches more or less. One end of the instrument is formed as a hand grip 2. The hand grip 2 of the needle guide 1 is curved to facilitate gripping and positioning of the opposite needle guide end 3.

The needle guide end 3 is best illustrated in FIG. 2, which shows a preferred embodiment in the form of a tube with the top of the tube cut away to provide the rounded guiding surface 4 for a suture needle. The tip 5 of the guide end 3 is rounded permitting its center to be positioned immediately at the point of the suturing. The curved and rounded tip 5 permits a soft yet firm contact with the point of suture entry. The guide end 3 for a typical instrument useful in hiatal hernia or similar operations has a needle guide surface 4 of some 1½ inches formed in the tubular needle guide material, such as a ½ inch diameter tube. An overall shape for the needle guide, which has proven satisfactory, is the generally "S" shaped form as illustrated in FIG. 1 and which facilitates the positioning of the guide end 3 while providing a firm grip for the surgeon.

FIGS. 3 thru 5 diagramatically illustrate steps in a hiatal hernia procedure with an uncut but stapled gastroplasty with the sutures 6 shown in FIG. 5 is position behind, around and about an uncut gastroplasty.

FIGS. 6 and 7 are perspective views illustrating the insertion of sutures 6 as guided by the needle guide 1 of the invention. FIG. 6 illustrates the needle guide 1 initially inserted at the point of suturing so that the exact point of needle 7 entry may be located behind or beneath uncut gastroplasty with the tapered end of the instrument in a position controlled by but not under the direct observation of the surgeon. When the needle guide 1 has been inserted to the position illustrated in FIG. 6, it is only inserted to manipulate the end of the needle 7 by the needle guide 1.

FIG. 7 shows the further use of the needle 7 using suitable forceps 8 to pass the needle 7 in and through the sutured surface.

It will therefore be seen that the needle guide of the invention permits a surgeon to accurately position and manipulate a suturing needle without having to resort to extensive cutting in the case of hiatal hernia operations or other portions of tissue or organs in this general field of surgery such as during pelvic surgery.

As various changes may be made in the form, construction and arrangement of the parts herein without departing from the spirit and scope of the invention and without sacrificing any of its advantages, it is to be understood that all matter herein is to be interpreted as illustrative and not in a limiting sense.

I claim:

1. A needle guide instrument for guiding a suturing needle comprising the combination of:
    an elongated member having a general longitudinal axis and having a gripping handle at one end;
    a suturing needle guide at the other end having an exposed concave needle guiding surface terminating in a rounded tip said needle guide being sufficiently rigid that said guiding surface will function for directing and for positioning the advancement of a suture needle in the general direction of the elongated member; and
    said gripping handle being elongated curved along its length away from said longitudinal axis for facilitating the gripping and positioning of the needle guide.

2. The guide instrument as claimed in claim 1 in which said suturing needle guide has a width of about one-half inch and a length of about one and one-half inch.

* * * * *